(12) United States Patent
Vering et al.

(10) Patent No.: US 8,352,196 B2
(45) Date of Patent: Jan. 8, 2013

(54) ASSESSMENT METHOD TO PROCESS A GLUCOSE CONCENTRATION SIGNAL AND DEVICES THEREOF

(75) Inventors: Thomas Vering, Bremgarten (CH); Florian Kuhnl, Rohrbach (CH); Lucas Kalt, Muenchenbuchsee (CH); Catalin Cris, Wuennewil (CH); Caroline Patte, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 13/267,436

(22) Filed: Oct. 6, 2011

(65) Prior Publication Data

US 2012/0029833 A1 Feb. 2, 2012

Related U.S. Application Data

(63) Continuation of application No. 12/511,190, filed on Jul. 29, 2009, now Pat. No. 8,060,318, which is a continuation of application No. PCT/CH2008/000025, filed on Jan. 25, 2008.

(30) Foreign Application Priority Data

Jan. 29, 2007 (EP) .................................. 07405024

(51) Int. Cl.
*G06F 19/00* (2011.01)
*A61B 5/00* (2006.01)
(52) U.S. Cl. .......................................... 702/19; 600/365
(58) Field of Classification Search .................... 702/19; 600/365
See application file for complete search history.

(56) References Cited

U.S. PATENT DOCUMENTS

2003/0208113 A1 11/2003 Mault et al.
2004/0193031 A1* 9/2004 Fuller ........................... 600/365

FOREIGN PATENT DOCUMENTS

EP 1 338 295 A1 2/2003
WO 00/74753 A1 12/2000

OTHER PUBLICATIONS

Ludovic J. Chassin, et al., Grading System to Assess Clinical Performance of Closed-Loop Glucose Control, Diabetes Technology and Therapeutics, vol. 7, No. 1, 2005, pp. 72-82, 2005.
Robert S. Parker, et al., A Review of Control Algorithms for Noninvasive Monitoring and Regulation in Type 1 Diabetic Patients, IEEE Engineering In Medicine and Biology Magazine, vol. 20, No. 1, Jan. 2001, pp. 65-73, 2001.
International Search Report, Appl. No. PCT/CH2008/000025, May 21, 2008.

* cited by examiner

*Primary Examiner* — Bryan Bui
(74) *Attorney, Agent, or Firm* — Dinsmore & Shohl LLP

(57) ABSTRACT

Embodiments of an assessment method for processing a signal corresponding to a glucose concentration and performing a retrospective analysis includes the steps of: a) initiating a first trigger, wherein the first trigger defines the beginning of a segment of a continuous measurement of glucose concentration or define the first of a series of spot measurements of glucose concentration; b) collecting data of the continuous measurement or the series of spot measurements of glucose concentration to be analyzed, wherein the collected data relates to a glucose concentration excursion corresponding to a reaction to a relevant event such as a meal or physical activity; c) analyzing the collected data initiated by a second trigger, wherein the second trigger defines the end of the collected data to be analyzed, wherein a measure for a grading of the excursion is determined from the collected data, and d) displaying the result of the analysis.

20 Claims, 3 Drawing Sheets

Fig. 6

ASSESSMENT METHOD TO PROCESS A GLUCOSE CONCENTRATION SIGNAL AND DEVICES THEREOF

CROSS REFERENCE TO RELATED APPLICATIONS

This application is a continuation of patent application Ser. No. 12/511,190 filed Jul. 29, 2009, now U.S. Pat. No. 8,060,318 which is a continuation of International Application No. PCT/CH2008/000025 filed Jan. 25, 2008, which claims priority to EP Application 07405024.6 filed Jan. 29, 2007.

TECHNICAL FIELD

Embodiments of the invention relates to an assessment method to process a signal corresponding to a glucose concentration and perform a retrospective analysis, and further embodiments relate to a device programmed to perform such an assessment method.

BACKGROUND

Diabetes is a disease in which the body does not produce an adequate amount of insulin or does not properly respond to the insulin produced. This results in an unbalanced blood glucose concentration (hyper- or hypoglycemia) leading to severe consequences such as ketoacidosis (diabetic coma), vascular complications as well as loss of consciousness or seizures. In order to maintain a healthy blood glucose concentration, patients usually keep a strict diet in combination with selective boluses of insulin. A bolus of insulin needs to be adjusted to the individual human body to provide an appropriate amount and distribution of insulin. Whether or not the amount and distribution of insulin are appropriate strongly depends on several factors such as the quantity and type of food and physical activity, e.g., exercise, stress or illness. Hence, the necessary amount of insulin varies depending on the patient's physical condition. To respectively serve the appropriate amount of insulin, the patient's response to certain factors like a meal needs to be considered. In addition to the amount and distribution of an insulin bolus, the timing of the bolus is of particular importance.

Existing methods to deal with monitoring the glucose concentration usually comprise the use of spot monitoring of blood glucose with a strip meter or tape cassette or the use of a continuous blood glucose monitoring device. Further, it is known to display the measured data in the form of a glucose concentration excursion curve. This provides rather exact and complete but more or less raw data, which are complicated to be interpreted by a patient or his or her health care provider (HCP).

When conventional methods are applied, the patient or his or her HCP respectively gets information about the glucose concentration excursion of a predefined period of time, e.g., of the last 12 or 24 hours. Moreover, the measurements usually do not consider the individual timing of relevant events such as physical activities or eating habits of a patient but measure over a fixed and predetermined period of time.

Glucose concentration is a value which is influenced by parameters such as the amount, distribution and timing of a bolus of insulin as well as by meals or physical activities of the patient. Said conventional measuring methods can only show absolute values of the respective blood glucose concentration at a specific time or within a specific period of time without taking other parameters such as timing of a meal or physical activity into account.

Any predetermined and fixed timing of a continuous measuring cycle or spot measurement, which is not synchronized with all influences to the blood glucose concentration excursion, is unable to react to the patient's individual habits. An intuitive analysis of measured values therefore is not possible if only the previously described conventional measuring methods are used. Even though the fact that e.g., a meal has been ingested can be seen from the blood glucose concentration excursion, its precise timing does not come out of the measured data. Therefore, in order to consider this timing, a parallel log of events with their respective time becomes necessary.

Thus, applying conventional monitoring and analyzing methods, an efficient determination of the right choice of the amount, distribution and timing of a bolus with respect to a specific meal or a specific activity and the like is only possible if the patient shows a strict discipline in matters of nutrition, sports and other physical activities or if he or she adhers to a strict logging of any possibly influencing event.

For a useful therapy and regimen respectively, a wide knowledge of a specific human body's response to a bolus of insulin as well as to nutrition and physical activities is crucial. Therefore therapies which are based on averaged data or a fixed measurement program are not satisfyingly matching the needs and requirements of an individual patient.

SUMMARY

In one embodiment, an assessment method for processing a signal corresponding to a glucose concentration and performing a retrospective analysis is provided. The method comprises the steps of: a) initiating a first trigger, wherein the first trigger defines the beginning of a segment of a continuous measurement of glucose concentration or defines the first of a series of spot measurements of glucose concentration; b) collecting data of the continuous measurement or the series of spot measurements of glucose concentration to be analyzed, wherein the collected data relates to a glucose concentration excursion corresponding to a reaction to a relevant event such as a meal or physical activity; c) analyzing the collected data initiated by a second trigger, wherein the second trigger defines the end of the collected data to be analyzed, wherein a measure for a grading of the excursion is determined from the collected data, and d) displaying the results of the analysis.

Other embodiments, features, and combinations of features will be described in the application in conjunction with the drawings.

BRIEF DESCRIPTION OF THE DRAWINGS

The drawings used to explain the embodiments include the following.

DETAILED DESCRIPTION

Embodiments of the present invention are directed to a method as well as a device pertaining to the technical field initially mentioned, which allow an easy determination of the appropriate amounts, distributions and timings of insulin boluses in different situations with respect to each individual patient. Further embodiments are directed to simplifying the analysis of measured data, to allow a more flexible analysis and thus to enhance the individual usefulness of an assessment of a glucose concentration measurement.

According to one embodiment, the assessment method to process a signal corresponding to a glucose concentration includes performing a retrospective analysis of the measured data and comprises the steps of starting the assessment initiated by a first trigger, collecting the data to be analyzed, analyzing the collected data initiated by a second trigger and displaying the results of the analysis. This assessment method may be performed using a device which comprises a measuring device for collecting the data to be analyzed, a computing device for analyzing the collected data, a storage device for recording the collected data and the results of the analysis, a display for visualizing the analyzed data and a communication link for transmitting data between the measuring device and the computing/storage device and display, respectively.

By performing a user-triggered and retrospective analysis of data which have been collected in particular during or after a relevant event such as a meal or physical activity, the user has the opportunity of choosing the time period the analysis is performed for. This ensures that the analysis relates to a certain event-specific context and therefore enhances the usefulness of the assessment of a glucose concentration.

The assessment process can be initiated by a first trigger which should correspond to a situation that needs examination with respect to glucose concentration. Then the data collection is performed by using glucose concentration measuring methods that are known as such, in particular by using a continuous monitoring of glucose concentration, whereas the first trigger defines the beginning of a segment of the continuous measurement. Alternatively, data can be collected using spot monitoring of glucose concentration using a strip meter or a tape cassette, whereas the first trigger defines e.g., the first of a series of spot measurements. Then a second trigger initiates the analysis of the collected data. It can either cause the collection of data to be stopped or define the end of the collected data to be analyzed. Eventually, the results of the analysis can be displayed. It is also possible to simply store the analysis and display it later in time or in combination with other analyses.

The first and the second trigger of the assessment method can correspond to a user input, such as e.g., pressing a button, contacting a touch screen, activating a voice sensitive device or similar interactions.

The first as well as the second trigger can also correspond to a predetermined time. In some embodiments, a trigger can be used as the second one, meaning that the data collection is performed during a predefined time. This time can be deduced from medical aspects such as an average reaction time of the blood glucose level to a meal or, e.g., during an insulin therapy, the period of time that a bolus of insulin works. Using a predetermined time as a first trigger can be particularly useful if a regular event is monitored (e.g., regular meals).

Further, a certain value and/or a progression of a glucose concentration can be employed as a trigger. If it is of interest whether the glucose concentration exceeds or falls below a certain (maybe critical) value, e.g., in order to monitor the development of the glucose concentration, the collection process and analysis can meet this demand by starting to collect data and stopping to collect data, respectively, when such a value is reached. Also, a certain progression of the glucose concentration, e.g., a particularly flat or steep slope or a local minimum or maximum of the glucose concentration, can be used as a first and/or second trigger.

A signal of an external device such as e.g., an insulin pump, a blood glucose meter for spot measurements, a thermometer or a pulse monitor can be used as a trigger as well, providing a plurality of possible trigger events, e.g., corresponding to events that have a direct connection with insulin therapy or that relate to physiological parameters such as a certain and possibly predefined body temperature or heart rate.

In other embodiments, combinations of these possible triggers can be used such as e.g., a user input as a first trigger combined with a predetermined time of e.g., four hours after initiation of data collection as a second trigger. It is even possible to combine different conditions (e.g., a certain glucose concentration determined by CGM during a certain predetermined time interval) in such a way that the starting or stopping of data collection is triggered only when all conditions are fulfilled.

The assessment method can be applied to glucose concentration excursion data corresponding to a reaction to a relevant event such as e.g., a meal or physical activity. This is of particular interest during insulin therapy, providing an online feedback, a therapy support and/or an assessment for therapy optimization. By monitoring the glucose concentration excursion, the effect of the therapy can be determined and optimized, e.g., the assessment of previous events can show whether the amount of insulin or the timing of the respective bolus sufficiently matches with the individual human body. Therefore, by monitoring and analyzing such relevant events, future therapy can be improved. In order that a measured glucose concentration excursion curve can be compared with an estimated excursion curve, a grading measure can be determined from the collected data.

One criterion for a grading of a measured glucose concentration excursion comprises a discrete number of target gates. A target gate comprises an interval of values enclosing a center value, which may be defined by an estimated glucose concentration, corresponding to an optimum reaction of the human body to a certain challenge (meal, bolus, physical activity etc.). The width of a target gate can be defined by an absolute value or by a relative width i.e., relative to the center value. In particular, to achieve a more accurate grading in the sense of smaller steps between the respective grades, each target gate can be substituted by a set of target gates. A set of target gates comprises at least a first target gate of a first width and a second target gate of a second width. In one embodiment, there are more than two target gates in each set. Again the width of each target gate of the set of target gates can be given by an absolute value or by a relative width. The centers of the target gates of each set of target gates may lie on the very spot. It might also be advantageous to displace the centers of the target gates so the interval values of the glucose excursion of the corresponding grade are displaced. In particular this might be the case if a value of the estimated glucose concentration excursion e.g., is close to a critical value so a deviation in one direction is not as significant as a deviation in the opposite one.

In the case of single target gates, the grading criterion of the glucose concentration excursion further comprises the number of target gates which enclose the measured glucose concentration excursion curve. As each target gate stands for a certain (absolute or relative) deviation of a measured value from its corresponding estimated value, the grade of the measured glucose concentration excursion curve is the better, the more target gates enclose it. In case of sets of target gates, the criterion of a grading of the glucose concentration excursion comprises the number of the first gates, the second gates and optionally additional gates of other widths that enclose the glucose concentration excursion curve. The best grading is achieved if the smallest target gate of each set of target gates encloses the glucose concentration excursion curve.

A further criterion for a grading of a glucose concentration excursion comprises a band of relative target ranges, whereas the width of the relative target ranges is determined as being a percentage of the appropriate value of the estimated glucose concentration excursion. In particular, in order to gain a more accurate grading, in the sense of smaller steps between the respective grades, the band of relative target ranges can be substituted by a set of bands of relative target ranges, which comprises at least one first band of a first relative target range and one second band of a second relative target range and optionally further bands of relative target ranges of different widths. In one embodiment, each of the relative target ranges is centered on the estimated glucose concentration excursion curve. However, the centers of the bands of relative target ranges can also be displaced out of the estimated glucose concentration excursion curve where that might be advantageous.

In case of one band of relative target ranges this criterion further comprises the relative time during which the measured glucose concentration excursion curve is enclosed by the band of relative target ranges. In case of a set of bands of relative target ranges this criterion further comprises the relative time in which the measured glucose concentration excursion curve is enclosed by each band of relative target ranges. Similar to the above mentioned criterion of discrete target gates, the best grade is achieved when the measured glucose concentration curve is completely enclosed by the narrowest band of relative target ranges. More generally speaking, the longer the measured glucose concentration excursion curve is enclosed by a narrow band of relative target ranges, the better is its grading.

A further criterion for a grading of a glucose concentration excursion comprises the use of j-indices, whereas a j-index is calculated using the mean value as well as the standard deviation of a number of measured glucose concentrations. The resulting j-index indicates how the measured glucose concentration excursion is to be graded relative to the estimated glucose concentration excursion, i.e., one or several ranges of numbers of j-indices categorise the deviations of the measured glucose concentration excursion with respect to the estimated glucose concentration excursion.

The previously described grading of a measured glucose concentration excursion allows for an online feedback of a glucose concentration control. The quality/grading of the glucose concentration control can be determined by one of the previously described grading processes and displayed. Thus, due to the ability of determining the quality/grading of the glucose concentration control, the effect of parameters of the glucose concentration control such as the amount or distribution of insulin or the timing of a bolus can be monitored and corrected. This is in order to match the treatment with the reaction of the organism of an individual person and helps to optimize future treatments of that person.

The determination of the quality/grading of the glucose concentration control can be based on the number of glucose values which lie within a target gate relative to the total number of target gates. That means that the percentage of target gates which enclose the glucose concentration excursion relates to the grading of the glucose concentration control as the deviation of the measured glucose concentration excursion is compared with and graded with respect to an estimated ideal glucose concentration excursion curve. In particular, providing a more accurate determination of the quality/grading of the glucose concentration control, it can be based on the respective numbers of glucose values which lie within the target gates of the first width, second width and optionally other widths, respectively, relative to the total number of sets of target gates. Here, only the smallest target gate per set of target gates, which encloses the glucose concentration excursion curve, is considered because if a narrow target gate encloses the glucose concentration excursion curve, a wider target gate of the same set of target gates necessarily encloses the glucose concentration excursion curve as well. The overall determination of the quality/grading of the glucose concentration control is subsequently deduced from the respective percentage of first, second and optionally other target gates, which enclose the measured glucose concentration excursion curve.

Further, the determination of the quality/grading of the glucose concentration control can be based on the relative time where the glucose concentration excursion curve lies within the band of relative target range. This relative time stands for the percentage where the band of relative target range encloses the measured glucose concentration excursion curve, similar to the previously described percentage of target gates that enclose the glucose concentration excursion curve but with a much larger total number of target gates and therefore a quasi-continuous band of relative target range. In particular, to achieve a more accurate determination of the quality/grading of the glucose concentration control, it can be based on the relative time where the glucose concentration excursion curve lies within the first, second and optionally other bands of relative target ranges, respectively.

A device or arrangement, which is designed and programmed to perform an assessment method on a signal corresponding to a glucose concentration as previously described, comprises a measuring device for collecting the data to be analyzed. Such a measuring device can be e.g., a continuous glucose measuring device or a strip meter or tape cassette. A computing device can analyze the collected data in the previously described way and control the assessment process, respectively. Further, a storage device can be used for recording the collected data in particular during the collection process. Analyses performed by the computing unit can also be stored in the storage device for future reviews or further processing of the analyses. The analyzed and—if applicable—the stored data then can be visualized on a display providing an online feedback to the user. For transmission of data between the measuring device on the one hand and the computing device, storage device and display on the other hand, a communication link is comprised by the inventive glucose concentration processing device.

In another embodiment, the communication link for data transmission between the measuring device on the one hand and the computing device, storage device and display on the other hand is working automatically without user interaction. Thus, the components can communicate with each other independently, and each trigger e.g., by user input or other previously described incidents can be internally processed without the need of further user interaction.

In another embodiment, the previously described assessment processing device is capable of applying at least two criteria and/or methods for determining the grading of a glucose concentration excursion and the criterion and/or method can be chosen online by the user. This feature of the device helps to improve the assessment as the previously described criteria and/or methods show individual advantages and disadvantages for certain applications and patients, respectively. Furthermore, combining more than one criteria or methods, respectively, may lead to an even clearer picture. Thus, a device that offers a choice of different assessment methods or grading criteria is much more flexible than a device with a fixed and predefined assessment method.

Figure 1:
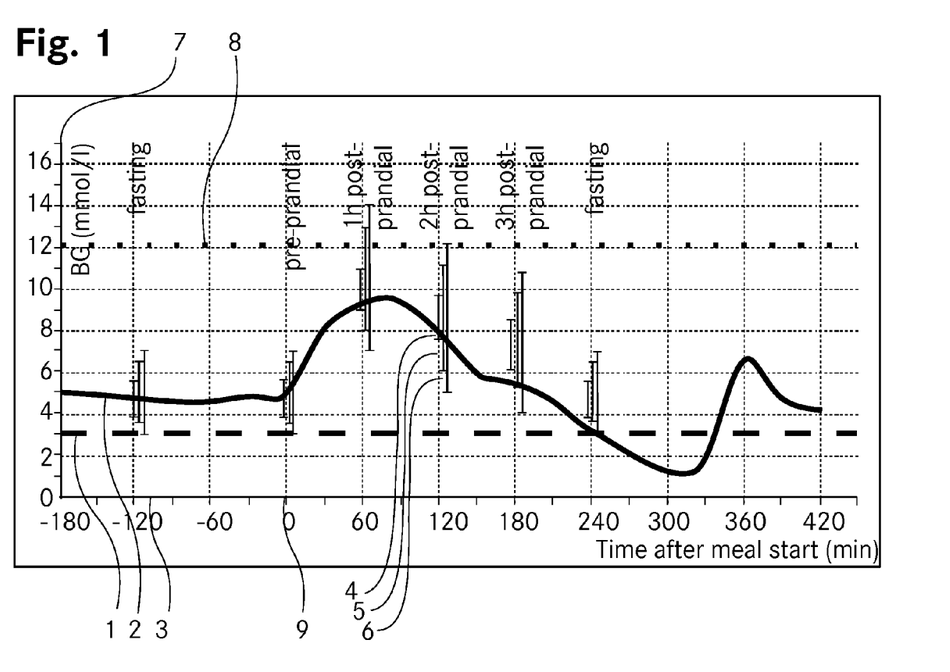
FIG. 1 is a diagram representing a blood glucose concentration excursion and a scheme of target gates according to one or more embodiments of the present invention.

FIG. 1 shows a diagram with its horizontal axis 3 annotated by time after a meal start 9 (in minutes) and its vertical axis 7 annotated by blood glucose concentration BG (in mmol/l). A measurement of a blood glucose concentration excursion 2 as well as thresholds of the critical blood glucose concentrations of hypoglycemia (threshold 1) and hyperglycemia (threshold 8) are plotted in the diagram. Several sets of target gates 4, 5, 6 indicate ranges of blood glucose concentrations around an ideal excursion. Target gates of a first width 4 define the smallest deviation of the measured glucose concentration excursion with respect to the ideal one. The target gates of second and third widths 5, 6 define further deviations of the measurement with respect to the ideal values. In the target gate method the measured data is downsampled to a few data points—in this example down to six points in time—to look at, which highly reduces the analysis effort.

Target gates of different widths 4, 5, 6 are defined at the same timed points along the glucose trace. They are further defined by their center point, which corresponds to an ideal glucose concentration at the respective timed point and a width towards higher and lower concentrations. A smaller width of a gate results in a better grading. In order to determine a grading for the blood glucose concentration excursion control, the grading of all sets of gates is taken into account.

A set of target gates comprises all equally timed target gates of different widths. In FIG. 1, the set corresponding to two hours (120 minutes) after meal start is given by the three gates 4, 5 and 6. Further sets of target gates are positioned at two hours before meal start (fasting), at meal start (pre-prandial), at one and three hours after meal start (post-prandial) and at four hours after meal start (fasting). The distribution of the sets of target gates is chosen with respect to the ideal glucose concentration excursion, but may be subject to change depending on the scope of the assessment of the blood glucose concentration excursion. Application of the target gate method does only consider discretely timed and meaningful points along the excursion curve.

The target gate method is triggered by the user, which is why this assessment method can be adapted to any individual patient's eating habits. Even without cyclic eating habits, a retrospective analysis of the blood glucose concentration control by a particular amount, timing and distribution of insulin can be performed as the analyzing process is triggered individually. At the end of the excursion, which typically occurs about four hours after the meal start, or at the user's next input, an online feedback can be given to the user. The feedback concerns the effect of the amount, timing and distribution of the insulin bolus, which has been applied with respect to the previous meal. This retrospective analyzing method does clearly determine how good the matching of the applied bolus of insulin to the specific meal was and thus gives advice for the further treatment.

Figure 2:
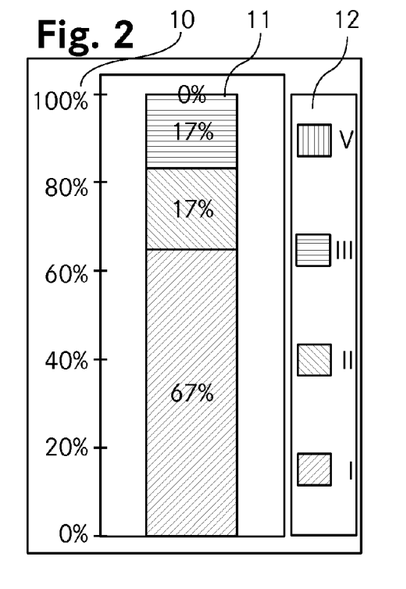
FIG. 2 is a diagram showing a distribution of grades determined by the target gates scheme according to one or more embodiments of the present invention.

In FIG. 2, the summarizing assessment of the blood glucose concentration control is shown. At the timed position of the target gates, the measured glucose concentration values are compared to the minimum and maximum values of the respective target gates. The best applicable grade, which is attributed to the narrowest gate that encloses the glucose concentration value, is assigned to the value of that timing. Subsequent application of this step results in a number of respective grades. The percentage of each grade with respect to the total number of grades, i.e., the total number of target gates, is shown in FIG. 2.

In FIG. 2, the summarized grading is shown as a column diagram 11, whereas the best grade I is plotted at the lowest position with the next best grade positioned on top of the first one and so on. A legend 12 shows the different grades, whereas I means the best grade (corresponding to the narrowest target gate), II and III the second and third best grade. V means that the measured glucose concentration value is not enclosed by a target gate and therefore indicates a lack of blood glucose concentration control. On the left hand side of the diagram there is a scale 10 showing percentages of 0% up to 100% for determining the accumulated percentage of a certain grade and better grades, e.g., 17% of the measurement were categorized grade II and III, respectively, as opposed to 67% of the measurement being categorized grade I. On the scale 10 an accumulated percentage of 84% of the measurement being categorized in grade II or better can be read.

Figure 3:
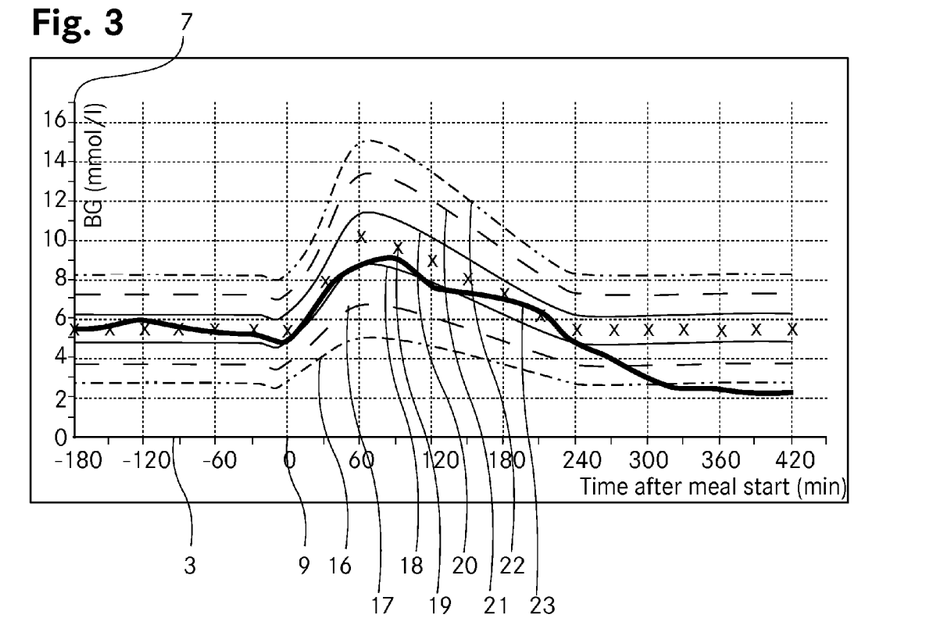
FIG. 3 is a diagram representing a blood glucose concentration excursion and a scheme of relative target ranges according to one or more embodiments of the present invention.

FIG. 3 shows a diagram with its horizontal axis 3 annotated by time after a meal start 9 (in minutes) and its vertical axis 7 annotated by blood glucose concentration BG (in mmol/l). A measurement of blood glucose concentration excursion 23 is plotted as well as a plurality of relative target ranges 16, 22; 17, 21; 18, 20 spaced from an ideal glucose concentration excursion depicted as crosses 19 to both sides. Each relative target range is defined by a width, which is relative to the center value given by the ideal glucose concentration 19. A first width of 25% relative to the ideal glucose concentration is represented by continuous lines 18, 20, a second width of 66%, by dashed lines 17, 21 and a third width of 100% is plotted as dashed-dotted lines 16, 22, whereas the recited widths are total widths meaning that a width of 25% corresponds to 12.5%, 66% to 33% and 100% to 50%, respectively, towards higher as well as lower values.

The relative target range method is similar to the target gate method but with a far greater number of target gates. Being a continuous or quasi-continuous assessment method, a more accurate determination of the quality of the glucose concentration excursion control is possible. This method therefore is particularly useful for continuous glucose concentration monitoring. As in the previously described target gate method, the assessment of the insulin regimen is performed either over a tuneable period of time or between two triggering events resulting from user input. A first trigger can start the assessment and data collection. The time of triggering can set the assumed time of meal start or another time before the time of meal start. The relative target ranges are subsequently arranged around the ideal glucose concentration excursion curve and the categorizing step is taking place during the measurement process. On a second trigger the result of the analyzing process is immediately shown to the user.

If the measured blood glucose concentration value lies within the first width of 25% it is categorized as a, within the second width of 66% as b, within the third width of 100% as c and if the values do not lie within a relative target range, they are categorized as d. These categories can directly be compared to those of the target gate method, whereas a is comparable to I, b to II, c to III and d to V.

The metric for the relative target range method for performing the summarized assessment of the blood glucose concentration excursion control is also similar to that of the target gate method. In one embodiment, as the number of gates goes to infinity, an enumeration is not preferred, instead, the respective period of time in which the curve is enclosed by each relative target range is chosen for being the basis for determining the percentage of the grading, i.e., the period of time spent by the measured curve within a relative target range is assigned to the corresponding grade. After finishing the measurement, the relative time in which the curve was enclosed by each relative target range denotes the fraction of the corresponding grade with respect to the total measurement. Assuming a measurement of 240 minutes, a summarized grading of 62% of grade a is achieved if the curve is enclosed by the narrowest relative target range for 149 minutes.

Figure 4:
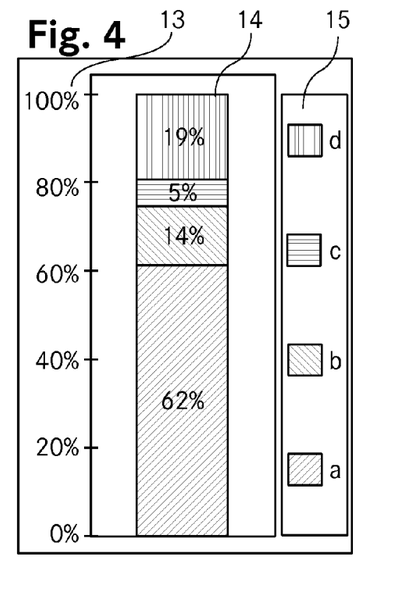
FIG. 4 is a diagram showing a distribution of grades determined by the relative target ranges scheme according to one or more embodiments of the present invention.

FIG. 4 corresponds to the result of the relative target range method as depicted in FIG. 3, whereas the relative target ranges 15 a to c correspond to the relative widths of 25%, 66% and 100% respectively. Target range d stands for a measured glucose concentration excursion which is separated from the ideal excursion by more than 100%, which is assumed as lack of glucose concentration excursion control. The column diagram 14 is similar to the column diagram 11 in FIG. 2. It shows the percentage of the respective relative target ranges. The scale 13 on the left hand side of the figure measures the accumulated percentage of a grade and all better grades, e.g., an accumulated percentage of 76% for grade b or better can be read from the scale 13 in connection with the column diagram 14.

Figure 5:
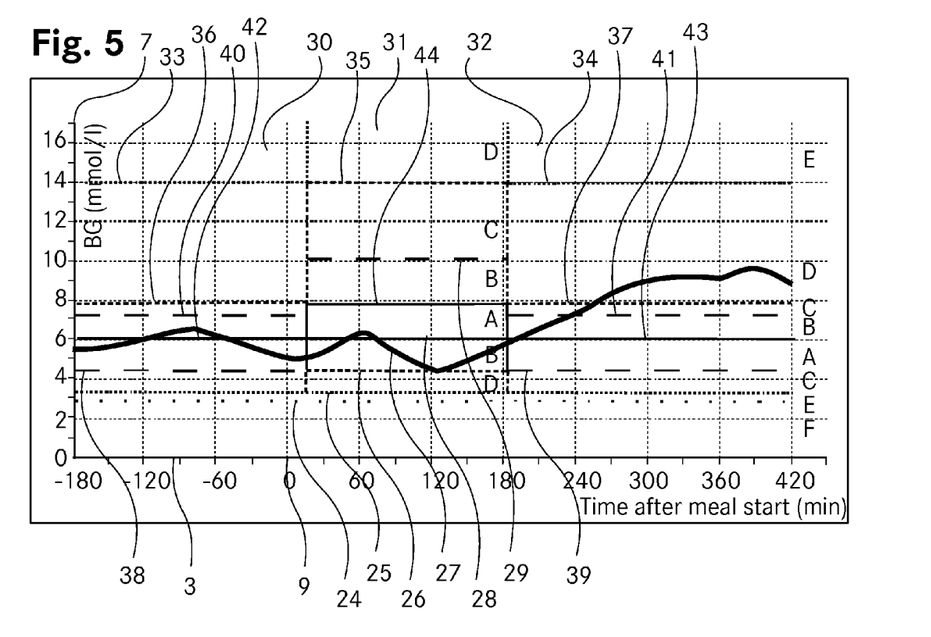
FIG. 5 is a diagram representing a blood glucose concentration excursion and a prandial/fasting grading scheme according to one or more embodiments of the present invention.

FIG. 5 shows a diagram with its horizontal axis 3 annotated by time after a meal start 9 (in minutes) and its vertical axis 7 annotated by blood glucose concentration BG (in mmol/l). A measurement of blood glucose concentration excursion 27 is plotted. This figure illustrates the prandial/fasting scheme as described in L. J. Chassin et al., "*Grading System to Assess Clinical Performance of Closed-Loop Glucose Control*", Diabetes Technology and Therapeutics 7 (2005) 72-82. The prandial/fasting scheme distinguishes the outside-meal condition (fasting) 30, 32 from the postprandial condition (prandial) 31, which is defined as a period of time of from 15 minutes to 180 minutes after meal ingestion. Each of the conditions represents a physiological status and defines threshold values for determination of the grade of a blood glucose concentration value.

The scheme comprises grades A to F, whereas A and B characterise excellent and good glucose control, respectively, without the need for a corrective action. Grade C represents suboptimal control with a recommendation for a corrective action. Grade D represents poor control requiring a corrective action. Grades E and F represent very poor and life-threatening control, respectively, with a need for an immediate corrective action or requiring an external assistance. Again, these grades can be looked at as corresponding directly to the previously described grades I to V and a to d, respectively. In contrast to the previously described assessment methods, the prandial/fasting scheme provides a simpler categorization with respect to time after meal start.

In FIG. 5 the grades are plotted as areas between lines of different shapes 24-29, 33-44. The following table may give an overview of said categories.

| Blood glucose concentration (BG) | Fasting condition | Prandial condition |
|---|---|---|
| ≦2.8 | F | F |
| ≦3.3 | E | E |
| ≦4.4 | C | D |
| ≦6.1 | A | B |
| ≦7.2 | B | A |
| ≦7.8 | C | A |
| ≦10.0 | D | B |
| ≦13.9 | D | C |
| ≦25 | E | D |
| >25 | F | F |

In the fasting condition there is no grade B or D in the hypoglycemic regime, whereas the prandial condition does not show a grade C in this regime as opposed to no grade E in case of hyperglycemia.

The metric for the summarized assessment of the blood glucose concentration excursion control is essentially the same as for the relative target range method, considering the respective period of time the curve is enclosed by each area as chosen for being the basis for determining the percentage of the grading, i.e., the period of time spent by the measured curve within an area is assigned to the corresponding grade. After finishing the measurement, the relative time in which the curve was enclosed by each area gives the fraction of the corresponding grade with respect to the total measurement.

Figure 6:
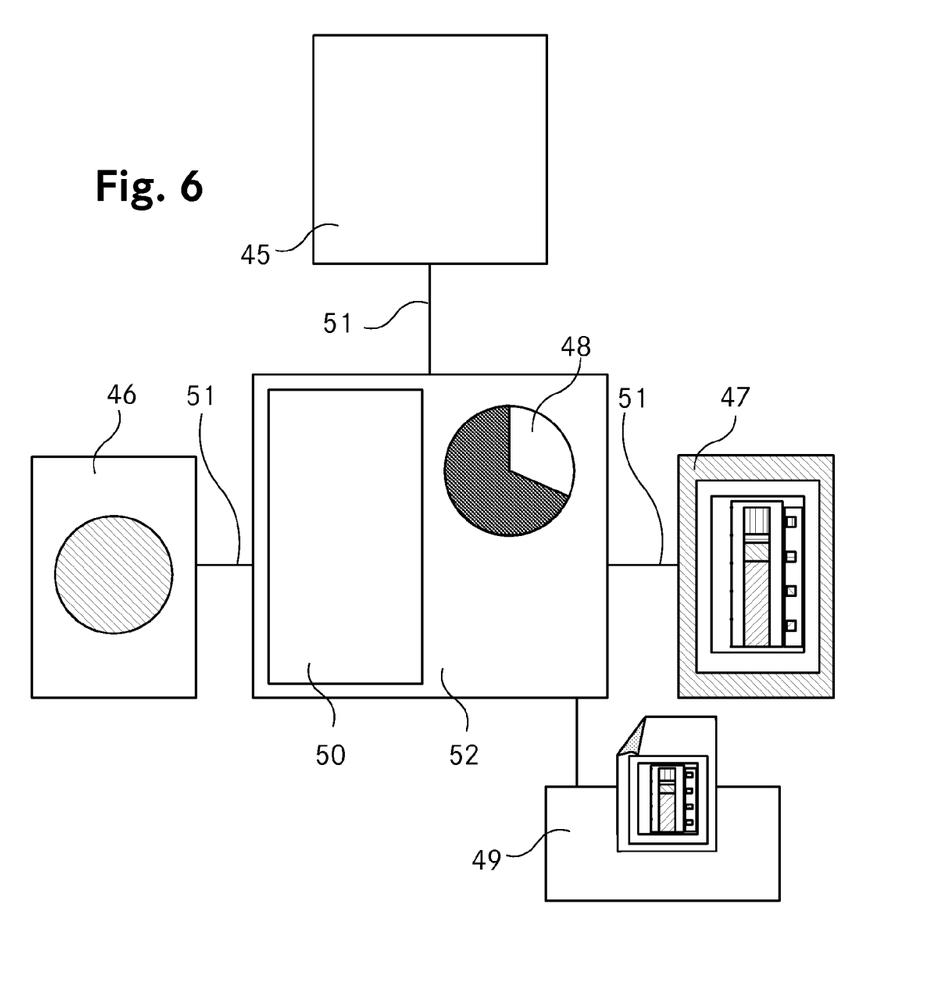
FIG. 6 is a schematic representation of a device for insulin therapy assessment according to one or more embodiments of the present invention.

FIG. 6 shows a device for performing the previously described assessment methods. It comprises a central unit 44, which coordinates the measurement and calculates the summarized assessment of the blood glucose concentration excursion control. It can be triggered by a user via a user interface 46 e.g., a button which defines the start of the measurement and/or the meal start. Triggered by the user input the central unit 44 starts assessment of the measurements, which are performed by a blood glucose concentration monitoring device 45 e.g., by spot monitoring of blood glucose concentration by a strip meter or cassette or by continuous monitoring of blood (or interstitial) glucose concentration. The measured data are processed by the central unit 44 using one of the previously described assessment methods. Either on a second trigger by the user or after a tunable period of time, which might be set by the user e.g., using a countdown 48, the results of the summarized assessment of the blood glucose concentration excursion control are displayed on a display device 47, these results can also be printed on a printer 49 that can be connected to the central unit 44.

In summary, it is to be noted that the previously described assessment schemes are a selection of a plurality of different methods to deal with grading of a glucose concentration excursion control. Other examples are the j-index (also j-value) method which leads to a grading by calculating a j-value using the definition $$j = 0.324 \cdot (\text{mean}(BG) + SD(BG))^2,$$

with mean(BG) being the mean of the measured blood glucose concentration (in mmol/l) and SD(BG) being the standard deviation of the blood glucose concentration (also in mmol/l). The actual grading subsequently is defined by ranges of j-values i.e., $10 < j < 20$ for ideal blood glucose concentration control up to $j > 40$ for lack of blood glucose concentration control. Other known assessment schemes such as pi-index method or determination of the area under the curve or incremental area under the curve, respectively, as well as those being further described in *Diabetes Techn. Therp.* 7 (2005) 72-82 by Chassin et al. can also be incorporated to the assessment device.

The assessment device as depicted in FIG. 6 can be modified e.g., in such a way that the user interface to trigger the assessment method as well as the display device can be combined in the central unit making the assessment device a single apparatus. The assessment device can also be combined with the measuring device e.g., in a closed-loop control of blood glucose concentration.

The number and meaning of the grading can be adapted to the scope of the assessment or therapy support. During optimization of the therapy the grading can be varied in such a way that the different grades get closer to one another as the optimization goes on, e.g., in the case of the target gate method all the gates can be made narrower and with less difference in width to each other in order to provide a finer grading of the therapy.

Triggering the assessment method can be done by a simple user input such as pressing a button. Other instruments for user input e.g., a touch screen on the display or a trigger using an external device can be employed. As for the second trigger, besides the same user input as that being used for the first one, a countdown may set the end of the assessment. In addition to these triggers by user input a triggering event can also be formed by a specific shape of the glucose concentration curve such as a steep slope or by a specific absolute value of the blood glucose concentration.

In order to observe and control proceedings in a diabetes therapy, the results of a plurality of assessments can be recorded and graphically displayed. This can also have a positive psychological effect on the patient as advances in the glucose concentration control and therefore in the efficiency of the therapy become apparent. The simple way of using the device enables any patient to perform an assessment of his/her actual glucose concentration excursion control. This in turn leads to a more reliable monitoring of the therapy and allows conclusion about the quality of the blood glucose concentration control. In particular a well-founded binary judgement in the sense of deciding on the therapy as being good or bad lies in the scope of the described assessment method.

In the Figs. and in the description above, the components may be referred to with the reference numbers listed below.

| List of Components | |
|---|---|
| 1 | Threshold for hypoglycemia |
| 2 | Glucose concentration curve |
| 3 | Time axis |
| 4 | Target gate |
| 5 | Target gate |
| 6 | Target gate |
| 7 | Blood glucose axis |
| 8 | Threshold |
| 9 | Time of meal start |
| 10 | Scale |
| 11 | Column diagram |
| 12 | Categories |
| 13 | Scale |
| 14 | Column diagram |
| 15 | Categories |
| 16 | Relative target range |
| 17 | Relative target range |
| 18 | Relative target range |
| 19 | Ideal glucose concentration |
| 20 | Relative target range |
| 21 | Relative target range |
| 22 | Relative target range |

-continued

| List of Components | |
|---|---|
| 23 | Glucose concentration curve |
| 24 | Threshold |
| 25 | Threshold |
| 26 | Threshold |
| 27 | Glucose concentration curve |
| 28 | Threshold |
| 29 | Threshold |
| 30 | Fasting regime |
| 31 | Prandial regime |
| 32 | Fasting regime |
| 33 | Threshold |
| 34 | Threshold |
| 35 | Threshold |
| 36 | Threshold |
| 37 | Threshold |
| 38 | Threshold |
| 39 | Threshold |
| 40 | Threshold |
| 41 | Threshold |
| 42 | Threshold |
| 43 | Threshold |
| 44 | Threshold |
| 45 | Measuring device |
| 46 | Trigger |
| 47 | Display |
| 48 | Countdown |
| 49 | Printer |
| 50 | Storing device |
| 51 | Communication link |
| 52 | Computing device |

What is claimed is:

1. An assessment method for processing a signal corresponding to a glucose concentration, comprising:
   providing a device comprising:
      a measuring device for collecting glucose concentration control data;
      a computing device coupled to the measuring device for analyzing the glucose concentration control data, the computer device being configured to both provide at least two target gates, each comprising an interval of values defined by an estimated glucose concentration corresponding to an optimum reaction of a human body to a challenge, and to determine a grade for the glucose concentration control;
   providing by the computing device the at least two target gates;
   collecting by the measuring device the glucose concentration control data;
   analyzing by the computing device the glucose concentration control data;
   determining by the computing device the grade for the glucose concentration control; and
   wherein the grading of the glucose concentration control is based on the number of glucose values which lie within at least one of the at least two target gates relative to the total number of target gates.

2. The method of claim 1 wherein the at least two target gates comprises a set of target gates comprising at least a first target gate of a first width and a second target gate of a second width.

3. The method of claim 1 wherein the at least two target gates comprises at least two sets of target gates comprising at least a first target gate of a first width and a second target gate of a second width.

4. The method of claim 1 wherein:
   at least one of the at least two target gates comprises at least one interval value having a center point corresponding to an ideal glucose concentration at a respective time point;

the center point is displaced so the interval values of the glucose excursion of the corresponding grade are displaced; and the computing device is additionally configured to account for the displaced centerpoint and displaced grading in determining the grade for the glucose concentration control.

5. The method of claim 4 wherein the computer is configured to account for a critical value in determining the grade for the glucose concentration control so a deviation in one direction is not as significant as a deviation in the opposite one.

6. The method of claim 1 wherein a monitoring device is coupled to the measuring device; and wherein collecting of data by the measuring device occurs when the monitoring device is triggered to communicate with the measuring device by a predetermined slope of a glucose concentration curve.

7. The method of claim 1 wherein a monitoring device is coupled to the measuring device, and wherein:
the monitoring device is a pulse monitor; and
the monitoring device is configured to have at least a first trigger starting measuring device data collection by the measuring device and at least a second trigger ending measuring device data collection wherein the first trigger corresponds with a first predefined heart rate and the second trigger corresponds to a second predefined heart rate, respectively; and wherein the predefined heart rates have a direct connection with insulin therapy.

8. The method of claim 7 wherein the at least first trigger starting data collection comprises the first predefined heart rate and a predefined temperature detected by a thermometer.

9. The method of claim 7 wherein the at least first trigger starting data collection comprises the first predefined heart rate, the predefined temperature, and a predetermined absolute blood glucose level.

10. A device for processing a signal corresponding to a glucose concentration comprising:
a measuring device for collecting glucose concentration control data; and
a computing device coupled to the measuring device, wherein the computing device is configured to:
analyze glucose concentration control data,
provide at least two target gates each comprising an interval of values defined by an estimated glucose concentration corresponding to an optimum reaction of a human body to a challenge and configured to determine a grade for the glucose concentration control; and
determine a grade for the glucose concentration control based on the number of glucose values which lie within at least one of the at least two target gates relative to the total number of target gates.

11. The device of claim 10 comprising a monitoring device configured to have at least a first trigger starting data collection by the measuring device and at least a second trigger ending data collection by the measuring device.

12. The device of claim 11 wherein the monitoring device is configured for quasi-continuous monitoring.

13. The device of claim 11 wherein the monitoring device is a pulse monitor.

14. The device of claim 11 comprising a thermometer and wherein the at least first trigger starting data collection comprises a predefined temperature.

15. The device of claim 11 wherein the monitoring device comprises a voice sensitive device configured to start and stop data collection by the at least first and second triggers, wherein the triggers are voice-mediated.

16. The device of claim 15 comprising a touch-sensitive screen coupled to the monitoring device configured to start and stop data collection by the measuring device based on user input using the touch screen.

17. The device of claim 10 comprising:
a display screen coupled to the computing device;
wherein the computing device is configured to account for non-cyclic eating habits by being configured to:
provide individual feedback to the user through the display screen at a predetermined time following the start of a meal;
wherein the feedback consists of the effect of the amount, timing and distribution of the insulin bolus, which has been applied with respect to the previous meal; and
wherein the computer is configured to determine how good the matching of the applied bolus of insulin to the specific meal was and thus gives advice for the further treatment.

18. A device for processing a signal corresponding to a glucose concentration comprising:
a monitoring device configured to have at least a first trigger starting data collection and at least a second trigger ending data collection;
a measuring device for collecting glucose concentration control data;
a computing device coupled to the measuring device, wherein the computing device is configured to:
analyze glucose concentration control data,
provide at least two target gates each comprising an interval of values defined by an estimated glucose concentration corresponding to an optimum reaction of a human body to a challenge and configured to determine a grade for the glucose concentration control, and
determine a grade for the glucose concentration control based on the number of glucose values which lie within at least one of the at least two target gates relative to the total number of target gates; and
a touch-sensitive screen coupled to the monitoring device configured to start and stop data collection by the monitoring device based on user input using the touch screen.

19. The device of claim 18 further comprising a display screen providing feedback to the user consisting of the determined grade for the glucose concentration.

20. The device of claim 18 wherein the computer is configured to account for a critical value in determining the grade for the glucose concentration control so a deviation in one direction is not as significant as a deviation in the opposite one.

* * * * *

UNITED STATES PATENT AND TRADEMARK OFFICE
CERTIFICATE OF CORRECTION

PATENT NO. : 8,352,196 B2
APPLICATION NO. : 13/267436
DATED : January 8, 2013
INVENTOR(S) : Thomas Vering et al.

It is certified that error appears in the above-identified patent and that said Letters Patent is hereby corrected as shown below:

Title page, item [75] Inventor name: "Florian Kuhnl" should read --Florian Kuhni--;
Title page, item [30] Foreign Application Priority Data: "EP 07405024" should read --EP 07405024.6--;
Title page, item [57] Abstract:
[57] "ABSTRACT
Embodiments of an assessment method for processing a signal corresponding to a glucose concentration and performing a retrospective analysis includes the steps of: a) initiating a first trigger, wherein the first trigger defines the beginning of a segment of a continuous measurement of glucose concentration or define the first of a series of spot measurements of glucose concentration;
b) collecting data of the continuous measurement or the series of spot measurements of glucose concentration to be analyzed, wherein the collected data relates to a glucose concentration excursion corresponding to a reaction to a relevant event such as a meal or physical activity; c) analyzing the collected data initiated by a second trigger, wherein the second trigger defines the end of the collected data to be analyzed, wherein a measure for a grading of the excursion is determined from the collected data, and d) displaying the result of the analysis."

Should read

[57] --ABSTRACT
Embodiments of an assessment method for processing a signal corresponding to a glucose concentration and performing a retrospective analysis includes the steps of: a) initiating a first trigger, wherein the first trigger defines the beginning of a segment of a continuous measurement of glucose concentration or defines the first of a series of spot measurements of glucose concentration;
b) collecting data of the continuous measurement or the series of spot measurements of glucose concentration to be analyzed, wherein the collected data relates to a glucose concentration excursion corresponding to a reaction to a relevant event such as a meal or physical activity; c) analyzing the collected data initiated by a second trigger, wherein the second trigger defines the end of the collected data to be analyzed, wherein a measure for a grading of the excursion is determined from the collected data, and d) displaying the results of the analysis.--;

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,352,196 B2

In the Specification

Col. 10, Lines 5-13, "≦" should read --•--;

Col. 2, Line 19, "adhers" should read --adheres--; and

Col. 11, Line 40, "judgement" should read --judgment--.

UNITED STATES PATENT AND TRADEMARK OFFICE
CERTIFICATE OF CORRECTION

PATENT NO. : 8,352,196 B2
APPLICATION NO. : 13/267436
DATED : January 8, 2013
INVENTOR(S) : Thomas Vering et al.

It is certified that error appears in the above-identified patent and that said Letters Patent is hereby corrected as shown below:

Title page, item [75] Inventor name: "Florian Kuhnl" should read --Florian Kuhni--;
Title page, item [30] Foreign Application Priority Data: "EP 07405024" should read
--EP 07405024.6--;
Title page, item [57] Abstract:
[57]                                         "ABSTRACT
Embodiments of an assessment method for processing a signal corresponding to a glucose concentration and performing a retrospective analysis includes the steps of: a) initiating a first trigger, wherein the first trigger defines the beginning of a segment of a continuous measurement of glucose concentration or define the first of a series of spot measurements of glucose concentration;
b) collecting data of the continuous measurement or the series of spot measurements of glucose concentration to be analyzed, wherein the collected data relates to a glucose concentration excursion corresponding to a reaction to a relevant event such as a meal or physical activity; c) analyzing the collected data initiated by a second trigger, wherein the second trigger defines the end of the collected data to be analyzed, wherein a measure for a grading of the excursion is determined from the collected data, and d) displaying the result of the analysis."

Should read

[57]                                         --ABSTRACT
Embodiments of an assessment method for processing a signal corresponding to a glucose concentration and performing a retrospective analysis includes the steps of: a) initiating a first trigger, wherein the first trigger defines the beginning of a segment of a continuous measurement of glucose concentration or defines the first of a series of spot measurements of glucose concentration;
b) collecting data of the continuous measurement or the series of spot measurements of glucose concentration to be analyzed, wherein the collected data relates to a glucose concentration excursion corresponding to a reaction to a relevant event such as a meal or physical activity; c) analyzing the This certificate supersedes the Certificate of Correction issued September 17, 2013.

Signed and Sealed this
Twenty-sixth Day of November, 2013

Margaret A. Focarino
*Commissioner for Patents of the United States Patent and Trademark Office* collected data initiated by a second trigger, wherein the second trigger defines the end of the collected data to be analyzed, wherein a measure for a grading of the excursion is determined from the collected data, and d) displaying the results of the analysis.--;

In the Specification

Col. 2, Line 19, "adhers" should read --adheres--;

Col. 10, Lines 5-13, "$\leqq$" should read --$\leq$--; and

Col. 11, Line 40, "judgement" should read --judgment--.